US006333058B1

(12) United States Patent
Ilavazhagan et al.

(10) Patent No.: US 6,333,058 B1
(45) Date of Patent: *Dec. 25, 2001

(54) PROCESS FOR THE PREPARATION OF A SPERMICIDAL AGENT

(75) Inventors: Govindaswamy Ilavazhagan; Chakra Devakumar, both of New Delhi (IN)

(73) Assignee: National Research Development Corporation, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/007,837

(22) Filed: Jan. 15, 1998

(51) Int. Cl.⁷ ........................ A61K 35/78; A61K 31/335; A01N 65/00
(52) U.S. Cl. ................................. 424/761; 424/DIG. 12; 424/DIG. 14; 514/450; 514/453; 514/783; 514/841; 514/842; 514/843
(58) Field of Search ...................................... 514/841–843, 514/450, 453, 783; 424/195.1, 761, DIG. 14, DIG. 12

(56) References Cited

U.S. PATENT DOCUMENTS

| H1541 | * | 6/1996 | Holla .................................. 424/195.1 |
| 4,946,681 | | 8/1990 | Walter ................................. 424/195.1 |
| 5,196,197 | | 3/1993 | Talwar et al. ....................... 424/195.1 |
| 5,395,951 | * | 3/1995 | Nagasampagi et al. ............. 549/383 |
| 6,083,506 | * | 7/2000 | Ilavazhagan et al. ............ 424/195.1 |

FOREIGN PATENT DOCUMENTS

| 2184564 A | 3/1997 | (CA) . |
| 2188110 A | 4/1997 | (CA) . |
| 3912059 A | 10/1990 | (DE) . |
| 0436257 A | 7/1991 | (EP) . |
| 0472791 A | 3/1992 | (EP) . |
| 0617119 A | 9/1994 | (EP) . |
| 0834254 A | 4/1998 | (EP) . |
| 2281511 A | 3/1995 | (GB) . |
| 171888 | * | 1/1993 | (IN) . |

OTHER PUBLICATIONS

Sinha, K.C. et al., "Neem oil as a vaginal contraceptive," Indian J. Med. Res., vol. 79, pp. 131–136 (Jan. 1984).*
Sinha, K.C. et al., "Anti–implantation effect of neem oil," Indian J. Med. Res., vol. 80, pp. 708–710 (Dec. 1984).*
Sharm, S.K. et al., "Mechanism of action of NIM–76: a novel vaginal contraceptive from neem oil," Contraception, vol. 54(6), pp. 373–378 (1996).*
U.S. application serial No. 09/014,703 filed on Jan. 28, 1998 and allowed on Dec. 29, 1999.
S. Garg et al., "Comparison of Extraction Procedures on the Immunocontraceptive Activity of Neem Seed Extracts", Journal of Ethnopharmacology, vol. 44, No. 2, Oct. 1994.
Biosis Abstract 1995: 39264 (1995).*
Page 1 from www. Neemfoundation.org/patents.htm, "Recent Indian Patents on Neem." 1997.*
Garg, S., "Comparison of Extraction Procedures on the Immunocontraceptive Activity of Neem Seed Extracts," Journal of Ethnopharmacology, vol. 44, pp. 87–92, 1994.
Chemical Abstracts 126: 84790 (Feb. 1997).*

* cited by examiner

*Primary Examiner*—John Pak
(74) *Attorney, Agent, or Firm*—Venable; Ashley J. Wells

(57) ABSTRACT

A process for preparing a spermicidal agent from neem oil includes (a) mixing neem oil with an aliphatic hydrocarbon solvent so that a precipitate forms, and filtering the mixture to separate the filtrate solution from the precipitate; (b) contacting the filtrate solution of step (a) with a polar extractant solvent whereby a spermicidal agent is extracted from the filtrate solution into the polar extractant solvent; and (c) removing solvent from the polar extractant solvent to produce a concentrated solution containing extract a spermicidal agent.

15 Claims, No Drawings

PROCESS FOR THE PREPARATION OF A SPERMICIDAL AGENT

BACKGROUND OF THE INVENTION

1. Field of the Invention

This invention relates to a process for the preparation of a spermicidal agent from neem oil or extractives. Though reference is made to a spermicidal agent, it is to be understood that such an agent also contains an antifertility agent.

2. Description of the Related Art

It is generally known that antifertility activity can be effected by three methods. One such method is that of a spermicidal activity by a spermicidal agent. Sperms from the male organism are killed or prevented from reaching the uterus of a female organism so as to prevent any fertilization. Yet another method is that the sperms are allowed to reach the uterus of a female organism. Such sperms are fertilized, and the fertilized ovum starts developing, and that the developing embryo travels to the wall of the uterus of a female organism and gets implanted.

In such a method the implantation is prevented. The third method is to allow the implantation and the uterine milieu is altered and embryo separated and aborted.

The present invention relates to a spermicidal agent so as to prevent a fertilization. Neem oil is known to have spermicidal activity, but its shelf life is short, and the activity too low to be of practical use. Thus, it is known to subject neem oil to the step of steam distillation to obtain a spermicidal agent. A disadvantage is that the process is time consuming, and the neem oil residues required for spermicidal activity are the residues obtained by the method of steam distillation become a waste.

Australian Patent No. 9,468,667 A discloses a method of blocking fertility in a male mammal by injecting neem oil or an active compound into the vas deferens of the male. U.S. Pat. No. 5,196,197 discloses an antifertility agent comprising neem oil and a reetha extract.

An object of this invention is to propose a process for the preparation of a spermicidal agent from neem oil and extractives.

Another object of this invention is to propose a process for the preparation of a spermicidal agent from neem oil and extractives which obviates the disadvantages associated with those of the prior art.

Yet another object of this invention is to propose a process for the preparation of a spermicidal agent from neem oil and extractives which has the required level of activity.

SUMMARY OF THE INVENTION

According to this invention there is provided a process for the preparation of a spermicidal agent from neem oil obtained from neem seeds comprising the steps of subjecting neem oil to the step of precipitation in the presence of an aliphatic hydrocarbon solvent, such as n-hexane, to obtain a precipitate containing essentially bitter constituents and a miscible solution containing odoriferous constituents, subjecting the miscible solution to the step of enrichment in the presence of a polar solvent to obtain a fraction comprising said solvent and said odiferous constituents, and distilling the polar solvent to obtain a concentrated extract enriched with spermicidal agent. The term neem oil used herein is intended to imply neem oil and neem extractives.

In accordance with this invention, neem oil is mixed with a solvent having a boiling point of up to 120° C. Preferably, the solvent comprises an aliphatic hydrocarbon such as n-hexane. The ratio of neem oil to solvent is 0.5:1 to 3:1. The solvent added to neem oil can be of light, middle or heavy fraction. Though all three fractions may be employed in the process of the present invention, it is preferred that the middle fraction be employed as the loss is less and the solvent can be recycled. If the light fraction is used, the boiling point is less than 60° C. and, consequentially, the cost is more in comparison to that of the middle fraction. The heavy fraction has a boiling point of 110 to 120° C. and, hence, greater energy is required for recovery of the solvent.

It is generally known that neem oil consists of glycerides, bitter and odiferous constituents. Only odiferous constituents are employed in the process of the present invention. Certain of such odiferous constituents that can be identified are 2-methyl-pentanal, ethyl propyldisulfide, 3,4-dimethylthiophene, Di-n-propyldisulfide, 2-phenylethanol, 1,2,3-trithracycle, hexane, 5-methyl-2-furturylfuran, trithiacyclononane, longifolene, (7) 8,9,10 (111)-tetrahydron, naptho (2,1-B)-thia, naphthene, 2-methyldecalm, nona-2,4-dienal, n-Propyl-cis-1-propenyl tetrasulfide, n-propyl-trans- 1-propenyl tetrasulfide, 2-Undecanone, 1,2-Bis (isopropyl-mercapto)ethane, Hexahydrofarnesol, methylpalmitate, ethylpalmitate, palmitic acid, farnesylacetate, methyl stearate, stearic acid, and ethyloleate.

The process of the present invention broadly consists in the steps of precipitation and enrichment. As described herein above, the step of solvent partition consists in adding an aliphatic hydrocarbon solvent to neem oil in the ratio of 1:1. The addition of solvent to neem oil provides a miscible solution consisting of glycerides, odoriferous and certain of the biter constituents. Such bitter constituents are removed by the step of precipitation, the remainder of the bitter constituents remaining in the solution.

The step of precipitation is carried out at room temperature. However, lower temperatures are preferred as this enhances the number of bitter constituents that precipitate from the solution. Thus, if the step of precipitation is effected at 10° C., it is estimated that as much as 50% of the bitter constituents are removed by precipitation. Preferably, the step of precipitation is carried out at a temperature of 0 to 15° C. The step of precipitation is carried out for a period of 15 to 60 minutes and preferably from 15 to 30 minutes.

After removal of the precipitation, the filtrate is subjected to the step of enrichment. For this purpose, the ratio of hydrocarbon solvent to the neem oil residue, after precipitation, is adjusted to a level so that the residue contains 0 to 75% for hydrocarbon solvent. The filtrate is either distilled off to remove excess hydrocarbon solvent or fresh excess hydrocarbon solvent is added to obtain the aforesaid condition. A polar extractant such as ethanol or methanol each containing 0 to 10% water is added to the filtrate.

Such a polar extractant is added to the filtrate in the ratio of 1:1 to 1:5 and preferably 1:3, and shaken to effect enrichment. The step of enrichment is carried out at a temperature of 10 to 40° C. and, for exarnple, in a separating vessel. Two layers are produced in the separating vessel. The upper layer is a hydrocarbon layer and contains most of the glycerides, which are not required in the spermicidal agent of the present invention. The lower layer is an alcohol layer containing the odiferous constituents and the remaining bitter constituents.

The lower layer is removed and fresh polar extractant is added to the upper layer. This step may be further repeated several times. Such a step of adding a polar solvent to the upper layer is repeated as a certain amount of odoriferous components are still retained in the upper layer. Thus, treatment with polar extractant allows a further separation of the odoriferous constituents from the upper layer. Alternatively, and in the instance where such a step of enrichment is carried out in a counter flow column, the extractant layer is recycled several times.

The lower layer obtained from the step of enrichment is then subjected to the step of distillation for removal of extractant under atmospheric pressure or moderate vacuum to obtain a concentrated extract.

Reference made herein above to a polar extractant is intended to imply a polar solvent containing 0 to 10% water.

DESCRIPTION OF THE PREFERRED EMBODIMENTS

Further objects and advantages of this invention will be more apparent from the ensuing example. However, it is to be understood that the ensuing example is not intended to imply any limitation on the scope of the invention.

EXAMPLE-1

To 50 g of neem oil, 100 ml of n-pentane was added. The liquid was swirled and the mixture chilled to 10 to 15° C. for 30 minutes. The solution of supernatant pentane was decanted and introduced into a separating funnel. The precipitate was dissolved in 10 ml of acetone and transferred to another flask where acetone was distilled to leave approx. 2 gms of the precipitate.

100 ml of aqueous methanol was added to the separating funnel containing the pentane solution of neem oil. After shaking, the lower layer containing aqueous methanol was drained. Such a step of separation was repeated thrice and the alcohol solutions thus obtained were pooled together and passed through a bed containing 50 gms. of anhydrous sodium sulfate in a funnel. The methanol was distilled off under reduced pressure of approximately 600 mm of Hg to leave behind a dark brown syrupy liquid. A spermicidal activity was found to be associated with this fraction.

Total Spermicidal Power: 1 ml of the emulsion of the spermicidal agent in saline at a concentration of 25 mg/ml was able to kill the spermatozoa in 0.8 ml of human semen (when added in 0.1 ml increments). The total spermicidal activity was estimated to be 100 mg of the agent for every 3 ml of monkey/human semen.

Spermicidal Activity of the Agent:

When the agent was instilled into the uterine horn it did not prevent pregnancy showing that it is devoid of any anti-implantation or abortifacient activity. (Table 2).

TABLE 2

Effect of intrauterine instillation of the agent in rats

| No. | No. of implants on control horn | No. of implants on exptl. Horm |
|---|---|---|
| 1. | 6 | 3 |
| 2. | 6 | 4 |
| 3. | 5 | 0 |
| 4. | 7 | 4 |
| 5. | 4 | 3 |
| 6. | 7 | 3 |

Rabbit Studies:

The precoital application of the agent impregnated in gelatin jelly in the case of rabbits showed that the spermicidal effect is dose dependent (Table-3). 15 mg of the agent per animal was able to inhibit pregnancy in all the animals completely, whereas 10 mg of the agent per animal was able to cause 67% inhibition and 5 mg was without any effect on fertility. The results show that the agent, by virtue of spermicidal activity, is able to inhibit pregnancy in rabbits when applied before coitus.

TABLE 3

Precoital spermicidal effect of the agent in rabbits

| Dose (mg). | No. of animals | No. of animals with implants | Spermicidal effect (%) |
|---|---|---|---|
| 5 | 6 | 6 | 0 |
| 10 | 6 | 2 | 67 |
| 15 | 6 | — | 100 |
| 20 | 6 | — | 100 |

Monkey Studies:

The intravaginal application of 150 mg of the agent was able to prevent pregnancy in monkeys when applied precoitally in the form of gelatin jelly and when mating occurred immediately after the application of the drug. Their menstrual cycle was not affected and the estradiol and progesterone levels did not show any change when compared with the control. The studies were repeated for three cycles in all the animals and there was no pregnancy. But in the control group where 1 ml of sterile jelly was applied, 60% of the females became pregnant which is the normal fertility rate in monkeys in captivity.

In-Vivo Precoital Spermicidal Activity of the Agent:

In this study it was found that 150 mg of the agent in 1 ml of jelly is able to kill all the sperms after mating (Table-4). This difference in the spermicidal activity from that of total spermicidal power mentioned earlier may be due to the presence of vaginal fluid which might have diluted the concentration of the agent and may also be due to the uneven distribution of the drug in the vagina. The above study also shows that the effect of the agent is does dependent. Approximately 150 mg of the agent is sufficient to kill all the spermatozoa after mating in monkey or human subjects.

TABLE 4

In vivo spermicidal activity of the agent in monkeys:

| Dose of drug | Monkey No. | | | | | |
|---|---|---|---|---|---|---|
| (mg/ml) | 1 | 2 | 3 | 4 | 5 | 6 |
| 50 | +++ | ++ | ++ | +++ | +++ | +++ |
| 100 | − | − | ++ | ++ | +++ | ++ |
| 125 | − | − | − | + | + | − |
| 150 | − | − | − | − | − | − |

Key
− No motility
+ <25% motile
++ 25 to 50% motile
+++ 50 to 80% motile
The agent was impregnated in 1 ml of gelatin jelly and applied near the cervix.

We claim:

1. A process for preparing a spermicidal agent from neem oil comprising:
   a) mixing neem oil with an aliphatic hydrocarbon solvent so that a precipitate forms, and filtering the mixture to separate the filtrate solution from the precipitate;
   b) contacting the filtrate solution of step (a) with a polar extractant solvent whereby a spermicidal agent is extracted from the filtrate solution into said polar extractant solvent; and c) removing solvent from said polar extractant solvent to produce a concentrated solution containing an extract enriched with spermicidal agent.

2. The process of claim 1 wherein the volume/volume ratio of said hydrocarbon solvent to neem oil in the precipitation step is in the range of from 1:2 to 3:1.

3. The process of claim 2 wherein the volume/volume ratio of said solvent to neem oil in the precipitation step is 1:1.

4. The process of claim 2 wherein the precipitation step is carried out at 0° C. to 15° C.

5. The process of claim 4 wherein the precipitation step is carried out for 15 to 60 minutes.

6. The process of claim 3 wherein the precipitation step is carried out at 0° C. to 15° C.

7. The process of claim 6 wherein the precipitation step is carried out for 15 to 60 minutes.

8. The process of claim 1 wherein said an aliphatic hydrocarbon solvent is selected from the group consisting of n-pentane and n-hexane.

9. The process of claim 1 wherein extraction step (b) comprises mixing the filtrate solution of step (a) with a polar extractant solvent, allowing the solutions to separate into two layers, removing the polar extractant solvent layer;

repeating the extraction one or more times, each time mixing the filtrate solution with fresh polar extractant solvent, allowing the two layers to separate, and removing the polar extractant solvent layer; and pooling said polar extractant solvent layers; and wherein concentration step (c) comprises removing solvent from said pooled polar extractant solvent layers to produce a concentrated solution containing a spermicidal agent.

10. The process of claim 1 wherein extraction step (b) comprises contacting the filtrate solution of step (a) with a polar extractant solvent in a counter flow column, wherein the polar extractant layer is recycled two or more times;

and wherein concentration step (c) comprises removing solvent from said recycled polar extractant solvent layer to produce a concentrated solution containing a spermicidal agent.

11. The process of claim 1 wherein said polar extractant solvent comprises an alcohol.

12. The process of claim 11 wherein said polar extractant solvent comprises an alcohol selected from the group consisting of ethanol and methanol, and the amount of water in said polar extractant solvent is in the range of from 0 to 10% by volume.

13. The process of claim 1 wherein the volume/volume ratio of said polar extractant solvent to said filtrate solution is in the range of from 1:1 to 1:5.

14. The process of claim 13 wherein the volume/volume ratio of said polar extractant solvent to said filtrate solution is 1:3.

15. The process of claim 1 wherein extraction step (b) is carried out at a temperature of 10° C. to 40° C.

* * * * *